United States Patent
Koh et al.

(10) Patent No.: US 11,118,236 B2
(45) Date of Patent: Sep. 14, 2021

(54) KIT AND METHOD FOR DETECTING HSV1 AND HSV2

(71) Applicant: Delta Electronics Int'l (Singapore) Pte Ltd, Singapore (SG)

(72) Inventors: Li Quan Koh, Singapore (SG); You Bin Lin, Singapore (SG); Weishi Zhang, Singapore (SG)

(73) Assignee: DELTA ELECTRONICS INT'L (SINGAPORE) PTE LTD, Singapore (SG)

( * ) Notice: Subject to any disclaimer, the term of this patent is extended or adjusted under 35 U.S.C. 154(b) by 386 days.

(21) Appl. No.: 16/056,016

(22) Filed: Aug. 6, 2018

(65) Prior Publication Data

US 2019/0249265 A1 Aug. 15, 2019

(30) Foreign Application Priority Data

Feb. 13, 2018 (SG) .............. 10201801233U

(51) Int. Cl.
| | | |
|---|---|---|
| *C12P 19/34* | (2006.01) | |
| *C12Q 1/70* | (2006.01) | |
| *C12Q 1/686* | (2018.01) | |
| *C12Q 1/6806* | (2018.01) | |
| *C12Q 1/6853* | (2018.01) | |

(52) U.S. Cl.
CPC .............. *C12Q 1/705* (2013.01); *C12Q 1/686* (2013.01); *C12Q 1/6806* (2013.01); *C12Q 1/6853* (2013.01); *C12Q 2600/112* (2013.01); *C12Q 2600/16* (2013.01); *C12Q 2600/166* (2013.01)

(58) Field of Classification Search
CPC ...... C12Q 1/705; C12Q 1/686; C12Q 1/6806; C12Q 1/6853
See application file for complete search history.

(56) References Cited

U.S. PATENT DOCUMENTS

2007/0141559 A1   6/2007   Exner
2014/0051590 A1   2/2014   Wu et al.

FOREIGN PATENT DOCUMENTS

WO      2016/071925 A2     5/2016

OTHER PUBLICATIONS

Rychlik et al., Nucleic Acids Research 17(21), 8543-8551 (1989). (Year: 1989).*
Lilly Namvar, "Detection and Typing of Herpes Simplex Virus (HSV) in Mucocutaneous Samples by TaqMan PCR Targeting a gB Segment Homologous for HSV Types 1 and 2", Journal of Clinical Microbiology, vol. 43, No. 5, May 2005, p. 2058-2064.
Paulo J. M. Bispo, "Rapid Detection and Identification of Uveitis Pathogens by Qualitative Multiplex Real-Time PCR", Investigative Ophthalmology & Visual Science, vol. 59, No. 1, Jan. 1, 2018, p. 582-589.

* cited by examiner

*Primary Examiner* — Kenneth R Horlick
(74) *Attorney, Agent, or Firm* — Kirton McConkie; Evan R. Witt

(57) ABSTRACT

A kit for simultaneously detecting HSV1 and HSV2 includes a forward primer and a reverse primer specific to HSV1, and a forward primer and a reverse primer specific to HSV2. The forward primer specific to HSV1 has a sequence of SEQ ID NO: 1 or SEQ ID NO: 4, and the reverse primer specific to HSV1 has a sequence of SEQ ID NO: 2 or SEQ ID NO: 7. The forward primer specific to HSV2 has a sequence of SEQ ID NO: 6, and the reverse primer specific to HSV2 has a sequence of SEQ ID NO: 7.

4 Claims, 10 Drawing Sheets

Specification includes a Sequence Listing.

| SEQ ID NO | Sequence (5' – 3') | Target | Orientation |
|---|---|---|---|
| 1 | AGGTGGACGAGATGCTGCGCT | HSV1 UL27 | Forward |
| 2 | GCGTTGTACCTGCGGGCGAAG | HSV1 UL27 | Reverse |
| 3 | CCGACGCCATATCCACCACCTTCACCACCA | HSV1 UL27 | Probe |
| 4 | TGTACGTGCGGGAACACCTCCG | HSV1 UL27 | Forward |
| 5 | CAAACCCCACGCCCCGCCGCC | HSV1 UL27 | Probe |
| 6 | CAGGACCGCAAGCCCCGGAATG | HSV2 UL27 | Forward |
| 7 | AAACTGCAGCCGGGCGAACTCG | HSV1/2 UL27 | Reverse |
| 8 | AGGCGCCCAGCGCCAACGCGTCC | HSV2 UL27 | Probe |

FIG. 1

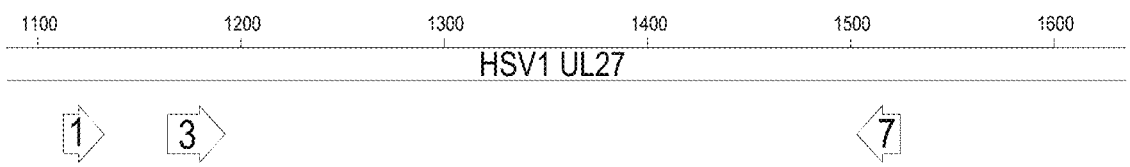
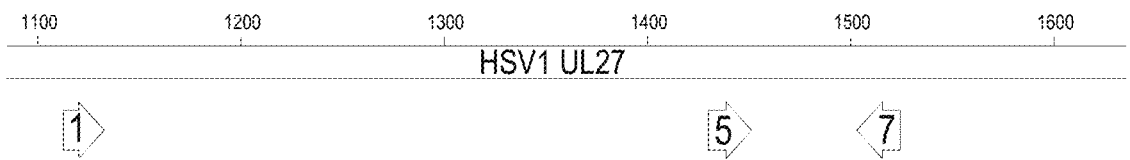
FIG. 2

| Plasmid DNA | Input amount | Cross Reactivity |
|---|---|---|
| pUC57 – OprL<br>*Pseudomonas aeruginosa* | $10^7$ cp | - |
| pUC57 – nuc<br>*Staphylococcus aureus* | $10^7$ cp | - |
| pUC57 – coa<br>*Staphylococcus aureus* | $10^7$ cp | - |
| pUC57 – HlyA<br>*Listeria monocytogenes* | $10^7$ cp | - |
| pUC57 – Tpi<br>*Closteridium difficile* | $10^7$ cp | - |
| pUC57 – cfb<br>*Streptococcus agalactiae* | $10^7$ cp | - |
| pUC57 – invA<br>*Salmonella typhimurium* | $10^7$ cp | - |
| pUC57 – ProA<br>*Pectobacterium carotovorum* | $10^7$ cp | - |
| pUC57 – Shr<br>*Arabidopsis thaliana* | $10^7$ cp | - |

FIG. 5A

| Genomic DNA | Input amount | Cross Reactivity |
|---|---|---|
| *Pseudomonas aeruginosa* | $5 \times 10^7$ cp | - |
| *Staphylococcus aureus* | $3 \times 10^7$ cp | - |

FIG. 5B

```
                              SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 1
aggtggacga gatgctgcgc t                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetically generated primer

<400> SEQUENCE: 2
gcgttgtacc tgcgggcgaa g                                              21

<210> SEQ ID NO 3
<211> LENGTH: 30
<212> TYPE: DNA
<213> ORGANISM: Artificial Sequence
<220> FEATURE:
<223> OTHER INFORMATION: Synthetically generated probe

<400> SEQUENCE: 3
ccgacgccat atccaccacc ttcaccacca                                     30

<210> SEQ ID NO 4
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 4
tgtacgtgcg ggaacacctc cg                                             22

<210> SEQ ID NO 5
<211> LENGTH: 22
<212> TYPE: DNA
<213> ORGANISM: Artificial Sequence
<220> FEATURE:
<223> OTHER INFORMATION: Synthetically generated probe

<400> SEQUENCE: 5
caaaccccac gcccccgccg cc                                             22

<210> SEQ ID NO 6
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 6
```

```
caggaccgca agccccggaa tg                                              22

<210> SEQ ID NO 7
<211> LENGTH: 22
<212> TYPE: DNA
<213> ORGANISM: Artificial Sequence
<220> FEATURE:
<223> OTHER INFORMATION: Synthetically generated primer

<400> SEQUENCE: 7
aaactgcagc cgggcgaact cg                                              22

<210> SEQ ID NO 8
<211> LENGTH: 23
<212> TYPE: DNA
<213> ORGANISM: Artificial Sequence
<220> FEATURE:
<223> OTHER INFORMATION: Synthetically generated probe

<400> SEQUENCE: 8
aggcgcccag cgccaacgcg tcc                                             23
```

KIT AND METHOD FOR DETECTING HSV1 AND HSV2

FIELD OF THE INVENTION

The present invention relates to a quick diagnosis of HSV1 and HSV2, and more particularly to kit and method for detecting HSV1 and HSV2.

BACKGROUND OF THE INVENTION

Herpes Simplex virus type 1 and 2 (HSV1 and HSV2) are members of the alpha herpesvirus subfamily, which contains a central core of double stranded DNA that is surrounded by a capsid. Of all the members in the alpha herpesvirus subfamily, HSV1 and HSV2 share the highest homology of approximately 50%. HSV1 and HSV2 are transmitted through oral and/or sexual contact, and can infect the mouth, genital tract and nervous system. One unique ability of herpesvirus is the ability to establish dormancy (or latency), and reactivate at a later stage.

HSV infections are endemic and persistent to infected individuals, with an estimated 67% of the population being infected with HSV1, and 11% of the population infected with HSV2. The symptoms of HSV infection ranges from painful blisters and ulcers at site of infection, to being largely asymptomatic in healthy individuals. HSV infections are most contagious when symptomatic, but asymptomatic carriers can also transmit HSV. In addition, HSV2 infected individuals are more likely to contract HIV, and HSV infections in immunocompromised individuals, such as HIV infected individuals, can lead to more severe complications, such as encephalitis, keratitis (for HSV1 infections); meningoencephalitis, esophagitis, hepatitis, pneumonitis, retinal necrosis or disseminated infection (for HSV2 infections). HSV infections can also be transmitted from mother to infant during delivery, and may lead to lasting neurologic disability or death in the infant. Therefore, the need to treat HSV infections and prevent HSV transmissions effectively points to the demand for a rapid, sensitive and specific diagnosis of HSV infections.

Currently, detection and diagnosis of HSV1 and HSV2 include viral culture assays, antigen-based assays and nucleic acid amplification assays. The viral culture assays are the traditional gold standards for HSV detections, based on staining of viral antigens with fluorescein-labeled antibody and examining for the presence of distinct fluorescence patterns or cytopathic effects of HSV by a trained individual. This detection method therefore requires a specialized, labour-intensive laboratory, and the test results can only be obtained in 2-7 days after sample collection. Furthermore, sample collection and transport conditions can affect the sensitivity of the viral culture tests, reducing the effectiveness in aiding the diagnosis.

The antigen-based assays such as HerpeSelect® 1 and 2 immunoblot are able to deliver results in approximately 4 hours. However, such kits require fresh samples, trained personnel, and multiple steps to obtain and validate the diagnosis. Furthermore, the antigen-based assays suffer from a possibility of false positive results due to antigen cross reactivity.

The best way to confirm HSV infections is molecular diagnosis, i.e. nucleic acid amplification assays, especially by polymerase chain reaction (PCR) testing. PCR is one of the methods that delivers not only sensitive, reliable, but also early detection of the infectious diseases agent. Nucleic acid amplification assays Artus® and Cobas® leverage on real-time PCR technology for the detection of HSV DNA. These assays offer higher reliability, sensitivity than the viral culture assays and the antigen-based assays, with also the advantage of ease of use and simultaneous testing of both HSV subtypes. As said assays leverage on the principles of PCR, where cycling of temperatures between 95° C. (30 seconds) for the denaturation of DNA, 50-60° C. (20 seconds) for the annealing of primers, and 72° C. (30-60 seconds) for the extension of primers allow for amplification of the nucleic acids to occur, these assays still involve a lengthy turnaround time (1 hour to 2 hours) prior to obtaining results.

Therefore, there is a need of providing an effective HSV diagnosis in order to overcome the above drawbacks.

SUMMARY OF THE INVENTION

An object of the present invention is to provide kit and method for simultaneously detecting HSV1 and HSV2 with high sensitivity, high specificity, and reduced reaction time.

Another object of the present invention is to provide kit and method for detecting HSV1 with high sensitivity, high specificity, and reduced reaction time.

An additional object of the present invention is to provide kit and method for detecting HSV2 with high sensitivity, high specificity, and reduced reaction time.

According to an aspect of the present invention, there is provided a kit for simultaneously detecting HSV1 and HSV2. The kit includes a forward primer and a reverse primer specific to HSV1, wherein the forward primer specific to HSV1 has a sequence of SEQ ID NO: 1 or SEQ ID NO: 4, a sequence with at least 80% sequence identity of SEQ ID NO: 1 or SEQ ID NO: 4, a sequence complementary to SEQ ID NO: 1 or SEQ ID NO: 4, or a sequence with at least 80% sequence identity of the sequence complementary to SEQ ID NO: 1 or SEQ ID NO: 4, and the reverse primer specific to HSV1 has a sequence of SEQ ID NO: 2 or SEQ ID NO: 7, a sequence with at least 80% sequence identity of SEQ ID NO: 2 or SEQ ID NO: 7, a sequence complementary to SEQ ID NO: 2 or SEQ ID NO: 7, or a sequence with at least 80% sequence identity of the sequence complementary to SEQ ID NO: 2 or SEQ ID NO: 7. The kit also includes a forward primer and a reverse primer specific to HSV2, wherein the forward primer specific to HSV2 has a sequence of SEQ ID NO: 6, a sequence with at least 80% sequence identity of SEQ ID NO: 6, a sequence complementary to SEQ ID NO: 6, or a sequence with at least 80% sequence identity of the sequence complementary to SEQ ID NO: 6, and the reverse primer specific to HSV2 has a sequence of SEQ ID NO: 7, a sequence with at least 80% sequence identity of SEQ ID NO: 7, a sequence complementary to SEQ ID NO: 7, or a sequence with at least 80% sequence identity of the sequence complementary to SEQ ID NO: 7. The forward primers and the reverse primers are used for real-time polymerase chain reaction. The kit further includes a probe having a sequence of SEQ ID NO: 3 or SEQ ID NO: 5, a sequence with at least 80% sequence identity of SEQ ID NO: 3 or SEQ ID NO: 5, a sequence complementary to SEQ ID NO: 3 or SEQ ID NO: 5, or a sequence with at least 80% sequence identity of the sequence complementary to SEQ ID NO: 3 or SEQ ID NO: 5 for specifically detecting HSV1. The kit further includes another probe having a sequence of SEQ ID NO: 8, a sequence with at least 80% sequence identity of SEQ ID NO: 8, a sequence complementary to SEQ ID NO: 8, or a sequence with at least 80% sequence identity of the sequence complementary to SEQ ID NO: 8 for specifically detecting HSV2.

According to another aspect of the present invention, there is provided a method for simultaneously detecting HSV1 and HSV2, the method comprising the step of amplifying DNA from HSV1 or HSV2 using real-time polymerase chain reaction with a forward primer and a reverse primer specific to HSV1 and a forward primer and a reverse primer specific to HSV2. The forward primers, the reverse primers and the probes used in the real-time polymerase chain reaction are the same as those described in the previous paragraph.

According to an additional aspect of the present invention, there is provided a kit for simultaneously detecting HSV1 and HSV2, which includes a forward primer specific to HSV1, a forward primer specific to HSV2, and a universal reverse primer specific to both HSV1 and HSV2, and also a method for simultaneously detecting HSV1 and HSV2, which includes the step of amplifying DNA from HSV1 or HSV2 using real-time polymerase chain reaction with a forward primer specific to HSV1, a forward primer specific to HSV2, and a universal reverse primer specific to both HSV1 and HSV2. The forward primer specific to HSV1 has a sequence of SEQ ID NO: 1 or SEQ ID NO: 4, a sequence with at least 80% sequence identity of SEQ ID NO: 1 or SEQ ID NO: 4, a sequence complementary to SEQ ID NO: 1 or SEQ ID NO: 4, or a sequence with at least 80% sequence identity of the sequence complementary to SEQ ID NO: 1 or SEQ ID NO: 4. The forward primer specific to HSV2 has a sequence of SEQ ID NO: 6, a sequence with at least 80% sequence identity of SEQ ID NO: 6, a sequence complementary to SEQ ID NO: 6, or a sequence with at least 80% sequence identity of the sequence complementary to SEQ ID NO: 6. The universal reverse primer specific to both HSV1 and HSV2 has a sequence of SEQ ID NO: 7, a sequence with at least 80% sequence identity of SEQ ID NO: 7, a sequence complementary to SEQ ID NO: 7, or a sequence with at least 80% sequence identity of the sequence complementary to SEQ ID NO: 7. A probe having a sequence of SEQ ID NO: 3 or SEQ ID NO: 5, a sequence with at least 80% sequence identity of SEQ ID NO: 3 or SEQ ID NO: 5, a sequence complementary to SEQ ID NO: 3 or SEQ ID NO: 5, or a sequence with at least 80% sequence identity of the sequence complementary to SEQ ID NO: 3 or SEQ ID NO: 5 is further included in the kit and used in the method for specifically detecting HSV1. Another probe having a sequence of SEQ ID NO: 8, a sequence with at least 80% sequence identity of SEQ ID NO: 8, a sequence complementary to SEQ ID NO: 8, or a sequence with at least 80% sequence identity of the sequence complementary to SEQ ID NO: 8 is further included in the kit and used in the method for specifically detecting HSV2.

According to a further aspect of the present invention, there is provided a kit for independently detecting HSV1 which includes a forward primer and a reverse primer, and also a method for detecting HSV1 which includes the step of amplifying DNA from HSV1 using real-time polymerase chain reaction with the forward primer and the reverse primer. The forward primer has a sequence of SEQ ID NO: 1 or SEQ ID NO: 4, a sequence with at least 80% sequence identity of SEQ ID NO: 1 or SEQ ID NO: 4, a sequence complementary to SEQ ID NO: 1 or SEQ ID NO: 4, or a sequence with at least 80% sequence identity of the sequence complementary to SEQ ID NO: 1 or SEQ ID NO: 4. The reverse primer has a sequence of SEQ ID NO: 2 or SEQ ID NO: 7, a sequence with at least 80% sequence identity of SEQ ID NO: 2 or SEQ ID NO: 7, a sequence complementary to SEQ ID NO: 2 or SEQ ID NO: 7, or a sequence with at least 80% sequence identity of the sequence complementary to SEQ ID NO: 2 or SEQ ID NO: 7. A probe having a sequence of SEQ ID NO: 3 or SEQ ID NO: 5, a sequence with at least 80% sequence identity of SEQ ID NO: 3 or SEQ ID NO: 5, a sequence complementary to SEQ ID NO: 3 or SEQ ID NO: 5, or a sequence with at least 80% sequence identity of the sequence complementary to SEQ ID NO: 3 or SEQ ID NO: 5 is further included in the kit and used in the method for specifically detecting HSV1.

According to a further aspect of the present invention, there is provided a kit for independently detecting HSV2 which includes a forward primer and a reverse primer, and a method for detecting HSV2 which includes the step of amplifying DNA from HSV2 using real-time polymerase chain reaction with the forward primer and the reverse primer. The forward primer having a sequence of SEQ ID NO: 6, a sequence with at least 80% sequence identity of SEQ ID NO: 6, a sequence complementary to SEQ ID NO: 6, or a sequence with at least 80% sequence identity of the sequence complementary to SEQ ID NO: 6. The reverse primer having a sequence of SEQ ID NO: 7, a sequence with at least 80% sequence identity of SEQ ID NO: 7, a sequence complementary to SEQ ID NO: 7, or a sequence with at least 80% sequence identity of the sequence complementary to SEQ ID NO: 7. A probe having a sequence of SEQ ID NO: 8, a sequence with at least 80% sequence identity of SEQ ID NO: 8, a sequence complementary to SEQ ID NO: 8, or a sequence with at least 80% sequence identity of the sequence complementary to SEQ ID NO: 8 is further included in the kit and used in the method for specifically detecting HSV2.

The above objects and advantages of the present invention become more readily apparent to those ordinarily skilled in the art after reviewing the following detailed description and accompanying drawings, in which:

BRIEF DESCRIPTION OF THE DRAWINGS

FIG. 1 shows the DNA sequences of the primers and the probes for detecting HSV1 and HSV2;

FIG. 2 shows the schematic views of the primer and probe annealing locations on the respective HSV sequence;

FIGS. 5A and 5B show the summarized results of cross reactivity tests with plasmid DNA and genomic DNA of other pathogens, respectively;

DETAILED DESCRIPTION OF THE PREFERRED EMBODIMENT

Figure 3:
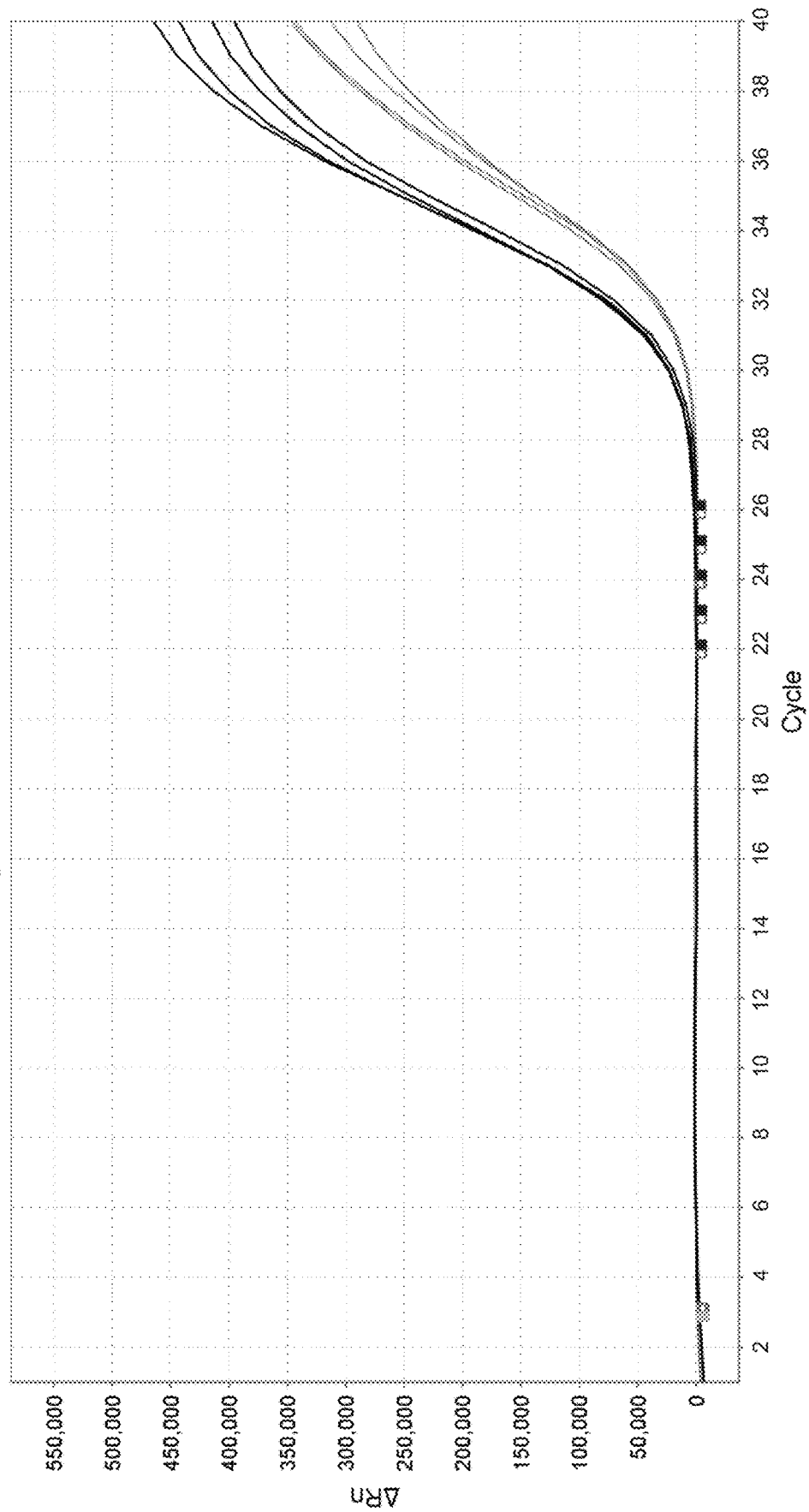
FIG. 3 shows the co-detection of 500 copies of HSV1 and HSV2 in a single reaction.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

The present invention utilizes real-time polymerase chain reaction (real-time PCR), also called quantitative polymerase chain reaction (qPCR), with probe-based detection for rapid, sensitive, specific and simultaneous diagnosis of HSV1 and HSV2 infections in humans. This is further complicated by the fact that the genes of HSV1 and HSV2 share 85% sequence similarities. In the present invention, Glycoprotein B (UL27) gene of HSV1 and HSV2 was selected as the target for the detection of the infectious agent. Primers are designed to target two different regions of the homologous gene in order to differentiate between the UL27 genes of HSV1 and HSV2.

The primers and the probes in the present invention allow for the rapid detection of HSV1 or HSV2 DNA through real-time PCR by optimizing design for reduction of ramping and extension timing per cycle, resulting in a shorter overall reaction time of at least 33%. The primers and the probes in the present invention also allow for the simultaneous or separate detection of HSV1 and HSV2 targets without compromising the sensitivity and specificity of each target.

In real-time PCR, the specific forward and reverse primers and probe hybridize to the DNA target of HSV1 or HSV2, wherein the probe is labeled with a 5'-reporter dye and a 3'-quencher. During PCR amplification, the probe is cleaved and the reporter dye and quencher are separated, so that the resulting increase in fluorescence can be detected. In an embodiment, the reporter dye is but not limited to FAM fluorescence, and the quencher is but not limited to BHQ1 group.

The DNA target, Glycoprotein B (UL27) gene for both HSV1 and HSV2, contains sufficient non-homology between HSV1 and HSV2 to provide for subtype specificity. The primer pairs were designed with a GC content of 60-70%, and a Tm of 65-68° C. The probes were designed with a GC content of 70-85%, and a Tm of 72-77° C. The target GC content for the amplicon amplified by the primer pairs were 60-70%, and 110-420 base pairs, preferably 110-190 base pairs.

FIG. 1 shows the DNA sequences of the primers and the probes for detecting HSV1 and HSV2. FIG. 2 shows the schematic views of the primer and probe annealing locations on the respective HSV sequence. For HSV1-specific primers and probes, the forward primer starts at position 1112 and includes 21-mer (5'-AGGTGGACGAGATGCTGCGCT-3'; SEQ ID NO: 1) or starts at position 1388 and includes 22-mer (5'-TGTACGTGCGGGAACACCTCCG-3'; SEQ ID NO: 4), the probe starts at 1163 and includes 30-mer (5'-CCGACGCCATATCCACCACCTTCACCACCA-3'; SEQ ID NO: 3) or starts at position 1430 and includes 22-mer (5'-CAAACCCCACGCCCCCGCCGCC-3'; SEQ ID NO: 5), and the reverse primer ends at 1292 and includes 21-mer (5'-GCGTTGTACCTGCGGGCGAAG-3'; SEQ ID NO: 2) or ends at 1524 and includes 22-mer (5'-AAACTGCAGCCGGGCGAACTCG-3'; SEQ ID NO: 7). For HSV2-specific primers and probe, the forward primer starts at position 1390 and includes 22-mer (5'-CAGGACCGCAAGCCCCGGAATG-3'; SEQ ID NO: 6), the probe starts at 1433 and includes 23-mer (5'-AGGCGCCCAGCGCCAACGCGTCC-3'; SEQ ID NO: 8), and the reverse primer ends at 1506 and includes 22-mer (5'-AAACTGCAGCCGGGCGAACTCG-3'; SEQ ID NO: 7). Among which, SEQ ID NO: 7 is a universal reverse primer specific to both HSV1 and HSV2.

Accordingly, for specifically detecting HSV1 UL27 gene, the forward primer could be SEQ ID NO: 1 or SEQ ID NO: 4, the reverse primer could be SEQ ID NO: 2 or SEQ ID NO: 7, and the probe could be SEQ ID NO: 3 or SEQ ID NO: 5.

In an embodiment, as shown in the combination A of FIG. 2, the forward primer of SEQ ID NO: 1, the reverse primer of SEQ ID NO: 2, and the probe of SEQ ID NO: 3 are used in a real-time PCR to amplify a region of HSV1 DNA with a size of 181 base pairs.

In an embodiment, as shown in the combination B of FIG. 2, the forward primer of SEQ ID NO: 4, the reverse primer of SEQ ID NO: 7, and the probe of SEQ ID NO: 5 are used in a real-time PCR to amplify a region of HSV1 DNA with a size of 130 base pairs.

In an embodiment, as shown in the combination C of FIG. 2, the forward primer of SEQ ID NO: 1, the reverse primer of SEQ ID NO: 7, and the probe of SEQ ID NO: 3 are used in a real-time PCR to amplify a region of HSV1 DNA with a size of 413 base pairs.

In an embodiment, as shown in the combination D of FIG. 2, the forward primer of SEQ ID NO: 1, the reverse primer of SEQ ID NO: 7, and the probe of SEQ ID NO: 5 are used in a real-time PCR to amplify a region of HSV1 DNA with a size of 413 base pairs.

For specifically detecting HSV2 UL27 gene, in an embodiment shown in the combination E of FIG. 2, the forward primer of SEQ ID NO: 6, the reverse primer of SEQ ID NO: 7, and the probe of SEQ ID NO: 8 are used in a real-time PCR to amplify a region of HSV2 DNA with a size of 117 base pairs.

Since the primers and the probes in the combinations A to D are specific for HSV1 detection and the primers and the probe in the combination E are specific for HSV2 detection, any one of the combinations A to D and the combination E could be used together for simultaneously and independently detecting HSV1 and HSV2 targets without compromising the sensitivity and specificity of each target.

In an embodiment, the combination A and the combination E are used for simultaneously detecting HSV1 and HSV2. That is, the forward primers of SEQ ID NOs: 1 and 6, the reverse primers of SEQ ID NOs: 2 and 7, and the probe of SEQ ID NOs: 3 and 8 are used in a real-time PCR to amplify a region of HSV1 DNA with a size of 181 base pairs and a region of HSV2 DNA with a size of 117 base pairs.

In an embodiment, the combination B and the combination E are used for simultaneously detecting HSV1 and HSV2. That is, the forward primers of SEQ ID NOs: 4 and 6, the universal reverse primer of SEQ ID NO: 7, and the probe of SEQ ID NOs: 5 and 8 are used in a real-time PCR to amplify a region of HSV1 DNA with a size of 130 base pairs and a region of HSV2 DNA with a size of 117 base pairs. Since the universal reverse primer of SEQ ID NO: 7 is used for both HSV1 and HSV2 detections, the number of the primers is reduced, which results in less complexity of the reaction.

In an embodiment, the combination C and the combination E are used for simultaneously detecting HSV1 and HSV2. That is, the forward primers of SEQ ID NOs: 1 and 6, the universal reverse primer of SEQ ID NO: 7, and the probe of SEQ ID NOs: 3 and 8 are used in a real-time PCR to amplify a region of HSV1 DNA with a size of 413 base pairs and a region of HSV2 DNA with a size of 117 base pairs. Since the universal reverse primer of SEQ ID NO: 7 is used for both HSV1 and HSV2 detections, the number of the primers is reduced, which results in less complexity of the reaction.

In an embodiment, the combination D and the combination E are used for simultaneously detecting HSV1 and HSV2. That is, the forward primers of SEQ ID NOs: 1 and 6, the universal reverse primer of SEQ ID NO: 7, and the probe of SEQ ID NOs: 5 and 8 are used in a real-time PCR to amplify a region of HSV1 DNA with a size of 413 base pairs and a region of HSV2 DNA with a size of 117 base pairs. Since the universal reverse primer of SEQ ID NO: 7 is used for both HSV1 and HSV2 detections, the number of the primers is reduced, which results in less complexity of the reaction.

To ascertain the specificity of the primers and the probes for HSV1 and HSV2, each of the primers and the probes listed in FIG. 1 was checked by NCBI BLAST, and the blast result shows that no other similar species have 100% same fragment compare to each of the primers and the probes of the present invention. The result demonstrates that the specificities of the primers and the probes are quite high, and the corresponding primer pair and the probe can be only used to amplify and detect HSV1 UL27 gene or HSV2 UL27 gene.

In some embodiments, the primers and the probes of the present invention are not limited to the ones having sequences totally the same as SEQ ID NOs: 1 to 8. For example, the primers and the probes have sequences with at least 80% sequence identity of SEQ ID NOs: 1 to 8 may possess similar specificity to the original ones and thus can also be used to detect HSV1 and HSV2. Particularly, the primers and the probes having sequences with at least 80% sequence identity of SEQ ID NOs: 1 to 8 and including the last 10-mer of SEQ ID NOs: 1 to 8 possess similar specificity to the original ones and thus can definitely be used to detect HSV1 and HSV2. In addition, the complementary sequence at the same location is capable of hybridizing to the other strand of the DNA, and thus can also be used as the primer or probe sequence. For example, in the combination A, the complementary sequence of SEQ ID NO: 1 and the complementary sequence of SEQ ID NO: 2 can be used as a primer pair for detecting HSV1. The other combinations B to E may also adapt similar modified embodiments, and are not redundantly described here. Therefore, the sequences complementary to SEQ ID NOs: 1 to 8, or the sequences with at least 80% sequence identity of the sequences complementary to SEQ ID NOs: 1 to 8 can also be used as the primers or the probes to detect HSV1 or HSV2.

In some other embodiments, since the primer pair, including the corresponding forward primer and reverse primer, is specific to HSV1 or HSV2, all the sequences located between the forward primer and the reverse primer may be used as the probe sequence, and thus, the probe sequence is not limited to the aforesaid sequence. Further, the probe may be designed to hybridize to any strand of the DNA, so both the complementary sequences at the same location may be used as the probe sequence. Therefore, the complementary sequence of the aforesaid probe sequence may also be used as the probe sequence for detecting HSV1 or HSV2.

Therefore, the present invention provides a kit for simultaneously detecting HSV1 and HSV2. The kit includes a forward primer and a reverse primer specific to HSV1, wherein the forward primer specific to HSV1 has a sequence of SEQ ID NO: 1 or SEQ ID NO: 4, a sequence with at least 80% sequence identity of SEQ ID NO: 1 or SEQ ID NO: 4, a sequence complementary to SEQ ID NO: 1 or SEQ ID NO: 4, or a sequence with at least 80% sequence identity of the sequence complementary to SEQ ID NO: 1 or SEQ ID NO: 4, and the reverse primer specific to HSV1 has a sequence of SEQ ID NO: 2 or SEQ ID NO: 7, a sequence with at least 80% sequence identity of SEQ ID NO: 2 or SEQ ID NO: 7, a sequence complementary to SEQ ID NO: 2 or SEQ ID NO: 7, or a sequence with at least 80% sequence identity of the sequence complementary to SEQ ID NO: 2 or SEQ ID NO: 7. The kit also includes a forward primer and a reverse primer specific to HSV2, wherein the forward primer specific to HSV2 has a sequence of SEQ ID NO: 6, a sequence with at least 80% sequence identity of SEQ ID NO: 6, a sequence complementary to SEQ ID NO: 6, or a sequence with at least 80% sequence identity of the sequence complementary to SEQ ID NO: 6, and the reverse primer specific to HSV2 has a sequence of SEQ ID NO: 7, a sequence with at least 80% sequence identity of SEQ ID NO: 7, a sequence complementary to SEQ ID NO: 7, or a sequence with at least 80% sequence identity of the sequence complementary to SEQ ID NO: 7. The forward primers and the reverse primers are used for real-time polymerase chain reaction. The kit further includes a probe having a sequence of SEQ ID NO: 3 or SEQ ID NO: 5, a sequence with at least 80% sequence identity of SEQ ID NO: 3 or SEQ ID NO: 5, a sequence complementary to SEQ ID NO: 3 or SEQ ID NO: 5, or a sequence with at least 80% sequence identity of the sequence complementary to SEQ ID NO: 3 or SEQ ID NO: 5 for specifically detecting HSV1. The kit further includes another probe having a sequence of SEQ ID NO: 8, a sequence with at least 80% sequence identity of SEQ ID NO: 8, a sequence complementary to SEQ ID NO: 8, or a sequence with at least 80% sequence identity of the sequence complementary to SEQ ID NO: 8 for specifically detecting HSV2.

The present invention also provides a method for simultaneously detecting HSV1 and HSV2. The method includes the step of amplifying DNA from HSV1 or HSV2 using real-time polymerase chain reaction with a forward primer and a reverse primer specific to HSV1 and a forward primer and a reverse primer specific to HSV2. The forward primers, the reverse primers and the probes used in the real-time polymerase chain reaction are the same as those described in the previous paragraph and thus are not redundantly described here.

Since SEQ ID NO: 7 is a universal reverse primer specific to both HSV1 and HSV2, the present invention also provides a kit for simultaneously detecting HSV1 and HSV2, which includes a forward primer specific to HSV1, a forward primer specific to HSV2, and a universal reverse primer specific to both HSV1 and HSV2, and a method for simultaneously detecting HSV1 and HSV2, which includes the step of amplifying DNA from HSV1 or HSV2 using real-time polymerase chain reaction with a forward primer specific to HSV1, a forward primer specific to HSV2, and a universal reverse primer specific to both HSV1 and HSV2. The forward primer specific to HSV1 has a sequence of SEQ ID NO: 1 or SEQ ID NO: 4, a sequence with at least 80% sequence identity of SEQ ID NO: 1 or SEQ ID NO: 4, a sequence complementary to SEQ ID NO: 1 or SEQ ID NO: 4, or a sequence with at least 80% sequence identity of the sequence complementary to SEQ ID NO: 1 or SEQ ID NO: 4. The forward primer specific to HSV2 has a sequence of SEQ ID NO: 6, a sequence with at least 80% sequence identity of SEQ ID NO: 6, a sequence complementary to SEQ ID NO: 6, or a sequence with at least 80% sequence identity of the sequence complementary to SEQ ID NO: 6. The universal reverse primer specific to both HSV1 and HSV2 has a sequence of SEQ ID NO: 7, a sequence with at least 80% sequence identity of SEQ ID NO: 7, a sequence complementary to SEQ ID NO: 7, or a sequence with at least 80% sequence identity of the sequence complementary to SEQ ID NO: 7. A probe having a sequence of SEQ ID NO: 3 or SEQ ID NO: 5, a sequence with at least 80% sequence identity of SEQ ID NO: 3 or SEQ ID NO: 5, a sequence complementary to SEQ ID NO: 3 or SEQ ID NO: 5, or a sequence with at least 80% sequence identity of the sequence complementary to SEQ ID NO: 3 or SEQ ID NO:

5 is further included in the kit and used in the method for specifically detecting HSV1. Another probe having a sequence of SEQ ID NO: 8, a sequence with at least 80% sequence identity of SEQ ID NO: 8, a sequence complementary to SEQ ID NO: 8, or a sequence with at least 80% sequence identity of the sequence complementary to SEQ ID NO: 8 is further included in the kit and used in the method for specifically detecting HSV2.

In addition, the present invention further provides a kit for independently detecting HSV1 which includes a forward primer and a reverse primer, and a method for detecting HSV1 which includes the step of amplifying DNA from HSV1 using real-time polymerase chain reaction with the forward primer and the reverse primer. The forward primer has a sequence of SEQ ID NO: 1 or SEQ ID NO: 4, a sequence with at least 80% sequence identity of SEQ ID NO: 1 or SEQ ID NO: 4, a sequence complementary to SEQ ID NO: 1 or SEQ ID NO: 4, or a sequence with at least 80% sequence identity of the sequence complementary to SEQ ID NO: 1 or SEQ ID NO: 4. The reverse primer has a sequence of SEQ ID NO: 2 or SEQ ID NO: 7, a sequence with at least 80% sequence identity of SEQ ID NO: 2 or SEQ ID NO: 7, a sequence complementary to SEQ ID NO: 2 or SEQ ID NO: 7, or a sequence with at least 80% sequence identity of the sequence complementary to SEQ ID NO: 2 or SEQ ID NO: 7. A probe having a sequence of SEQ ID NO: 3 or SEQ ID NO: 5, a sequence with at least 80% sequence identity of SEQ ID NO: 3 or SEQ ID NO: 5, a sequence complementary to SEQ ID NO: 3 or SEQ ID NO: 5, or a sequence with at least 80% sequence identity of the sequence complementary to SEQ ID NO: 3 or SEQ ID NO: 5 is further included in the kit and used in the method for specifically detecting HSV1.

Moreover, the present invention further provides a kit for independently detecting HSV2 which includes a forward primer and a reverse primer, and a method for detecting HSV2 which includes the step of amplifying DNA from HSV2 using real-time polymerase chain reaction with the forward primer and the reverse primer. The forward primer having a sequence of SEQ ID NO: 6, a sequence with at least 80% sequence identity of SEQ ID NO: 6, a sequence complementary to SEQ ID NO: 6, or a sequence with at least 80% sequence identity of the sequence complementary to SEQ ID NO: 6. The reverse primer having a sequence of SEQ ID NO: 7, a sequence with at least 80% sequence identity of SEQ ID NO: 7, a sequence complementary to SEQ ID NO: 7, or a sequence with at least 80% sequence identity of the sequence complementary to SEQ ID NO: 7. A probe having a sequence of SEQ ID NO: 8, a sequence with at least 80% sequence identity of SEQ ID NO: 8, a sequence complementary to SEQ ID NO: 8, or a sequence with at least 80% sequence identity of the sequence complementary to SEQ ID NO: 8 is further included in the kit and used in the method for specifically detecting HSV2.

The following describes an example of the method for detecting HSV1 and HSV2 of the present invention.

The real-time PCR was performed with Taqman probe based mastermix, 600 nM of each HSV specific Primer, 200 nM of HSV1-specific probe, 100 nM of HSV2-specific probe, in a total volume of 10 μL. FAST PCR cycling conditions were as follows, 95° C. for 30 seconds, followed by 40 cycles of denaturation at 95° C. for 1 second, and annealing and primer extension at 68° C. for 10 seconds.

It is noted that, due to the increased Tm and higher GC % of the designed primers, probes and amplicons, the present invention allows for amplification with 2-step PCR, i.e. the step of denaturation at 95° C. and the step of annealing/ extension at 68° C. In other words, the present invention allows for elevated annealing temperature, so the annealing step could be combined with the extension step, and thus eliminate a separate annealing step. Therefore, the present invention significantly reduces the ramping and extension time required per cycle in the thermocycler. This results in a reduction of the overall reaction time to less than 20 minutes from 1 hour using the conventional method. Hence, the present invention has the advantage of reduced reaction time, while maintaining the specificity and sensitivity of the assay.

Further, the present invention allows for the detection of both HSV1 and HSV2 DNA in the same reaction. FIG. 3 shows the co-detection of 500 copies of HSV1 and HSV2 in a single reaction. It is clear that HSV1 and HSV2 can be independently detected in the same reaction. Therefore, the present invention enables the rapid and simultaneous detection of HSV1 and HSV2.

Figure 4A:
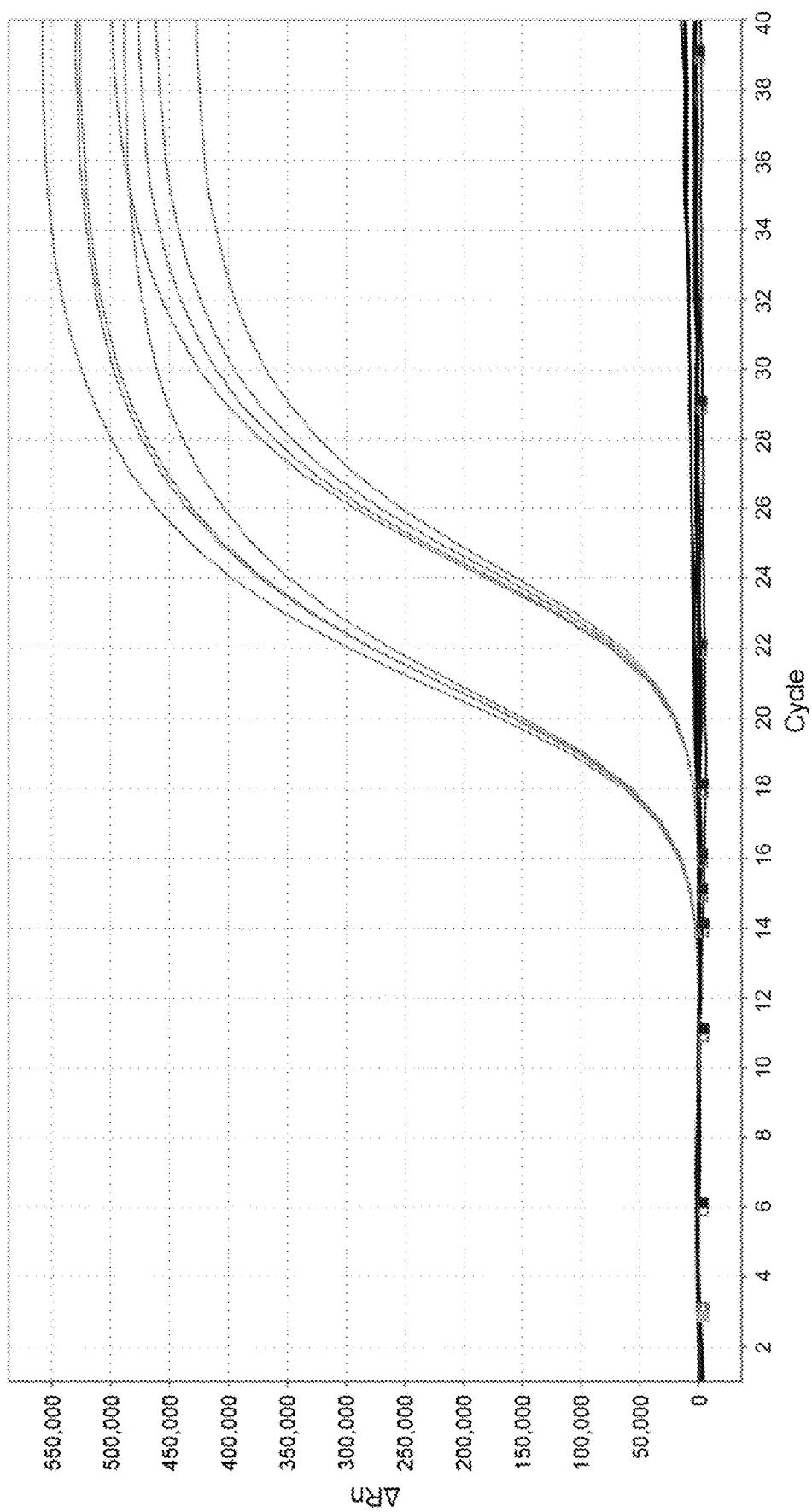
FIGS. 4A and 4B show no cross reaction between HSV1 and HSV2.
Figure 4B:
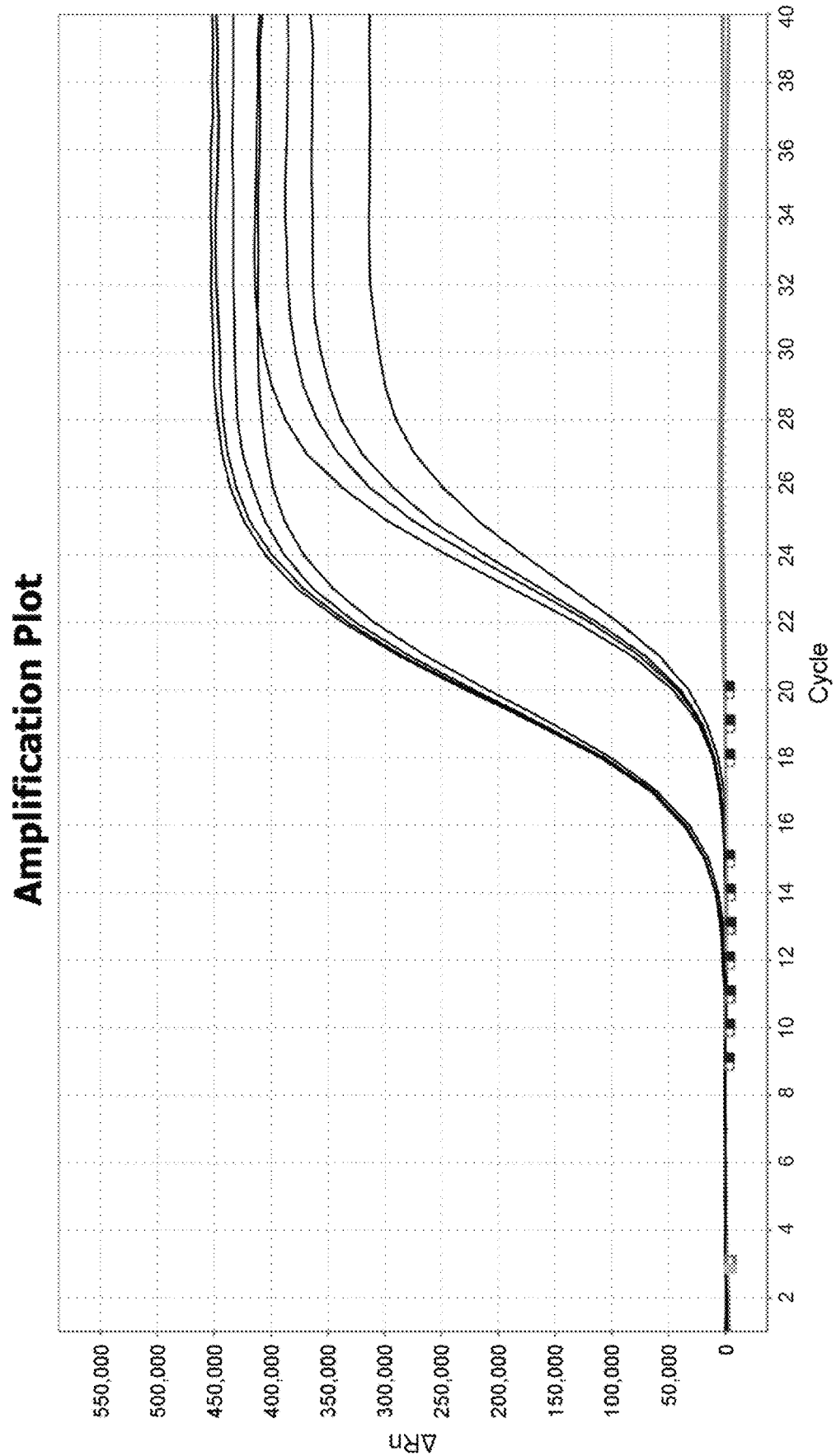

In addition, the present invention allows for the consistent and specific detection of HSV1 or HSV2 DNA using the rapid thermal profile. The primers were verified in silico through NCBI BLAST against human and human pathogen databases for a lack of cross reactivity to other alphaherpes virus, human and human pathogen DNA. FIGS. 4A and 4B show no cross reaction between HSV1 and HSV2. In FIG. 4A, when the HSV1 primers and the concentrated positive control ($10^6$-$10^7$ copies) of HSV2 were tested in a duplex reaction, only HSV1 was detected which did not show any cross reactivity in the other subtype of HSV2. While in FIG. 4B, when the HSV2 primers and the concentrated positive control ($10^6$-$10^7$ copies) of HSV1 were tested in a duplex reaction, only HSV2 was detected which did not show any cross reactivity in the other subtype of HSV1. Hence, the designed primers in the present invention are very specific.

Besides, the HSV1 or HSV2 primers and the concentrated positive controls of plasmid DNA and genomic DNA of other pathogens were also tested in a duplex reaction. As shown in FIGS. 5A and 5B, the HSV1 or HSV2 primers of the present invention shows no cross reactivity to other bacteria plasmids and genomic DNA.

Figure 6A:
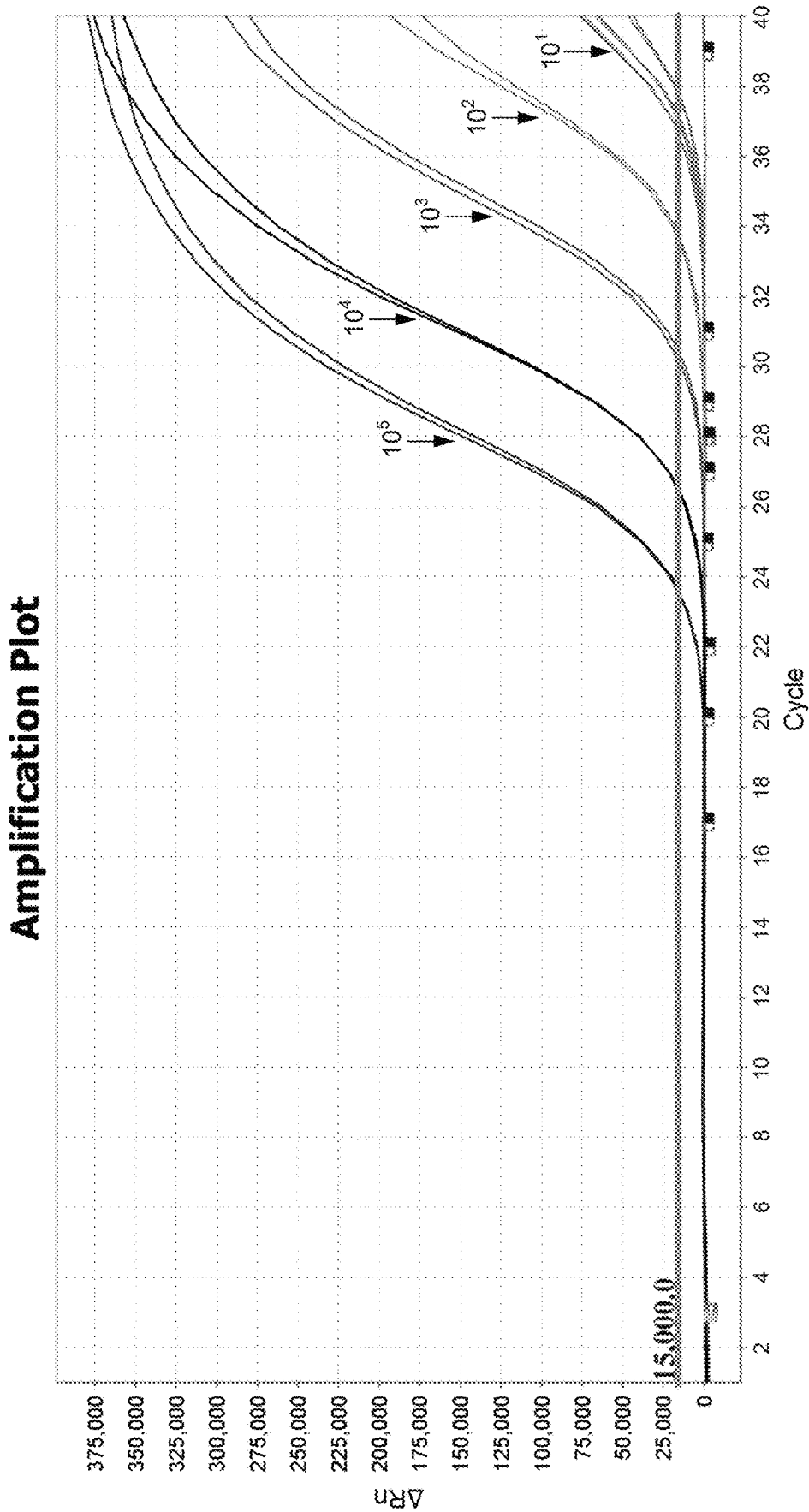
FIGS. 6A and 6B show the amplification of different copies of HSV1 and the corresponding linearity assay.
Figure 6B:
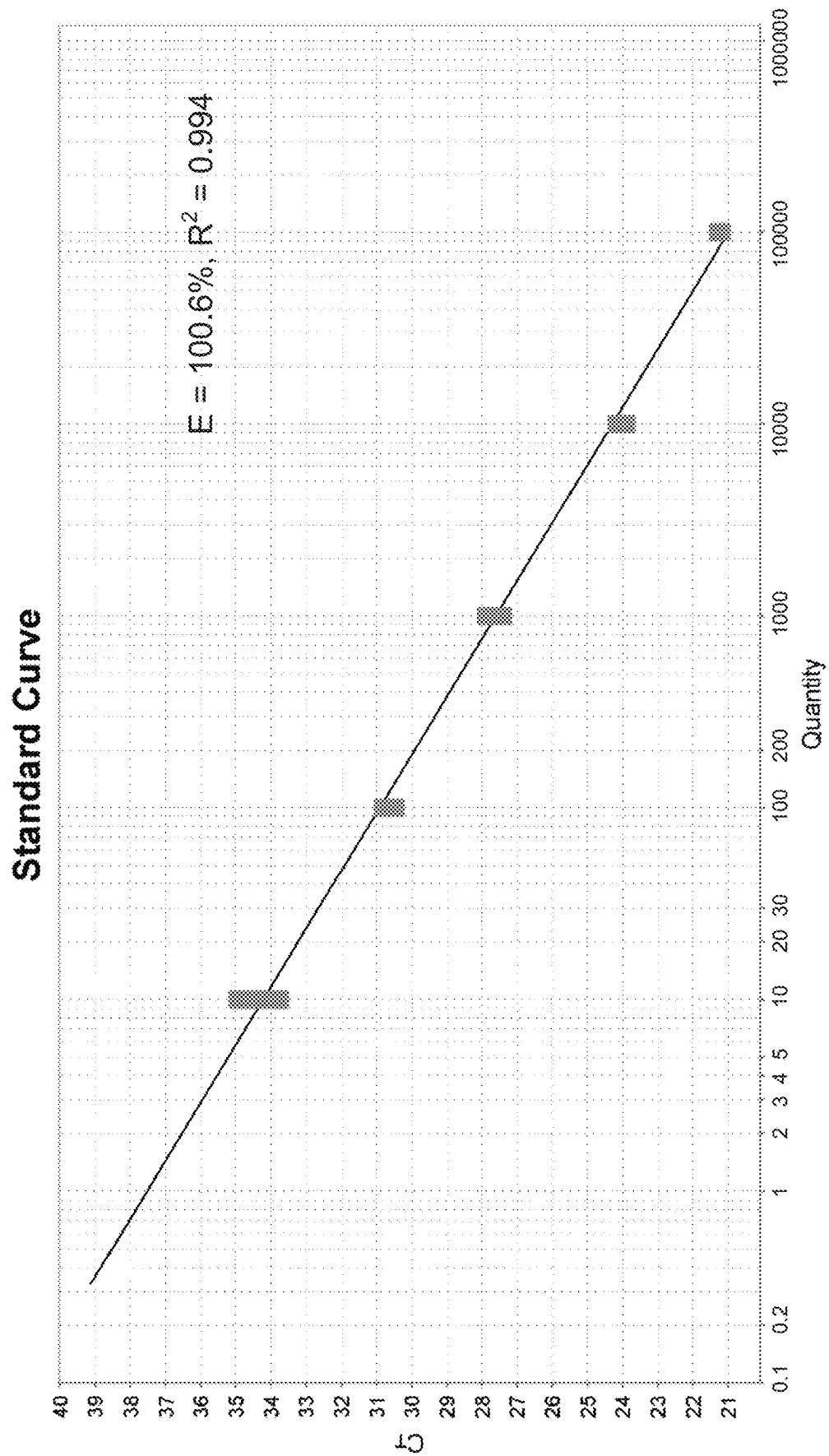
Figure 7A:
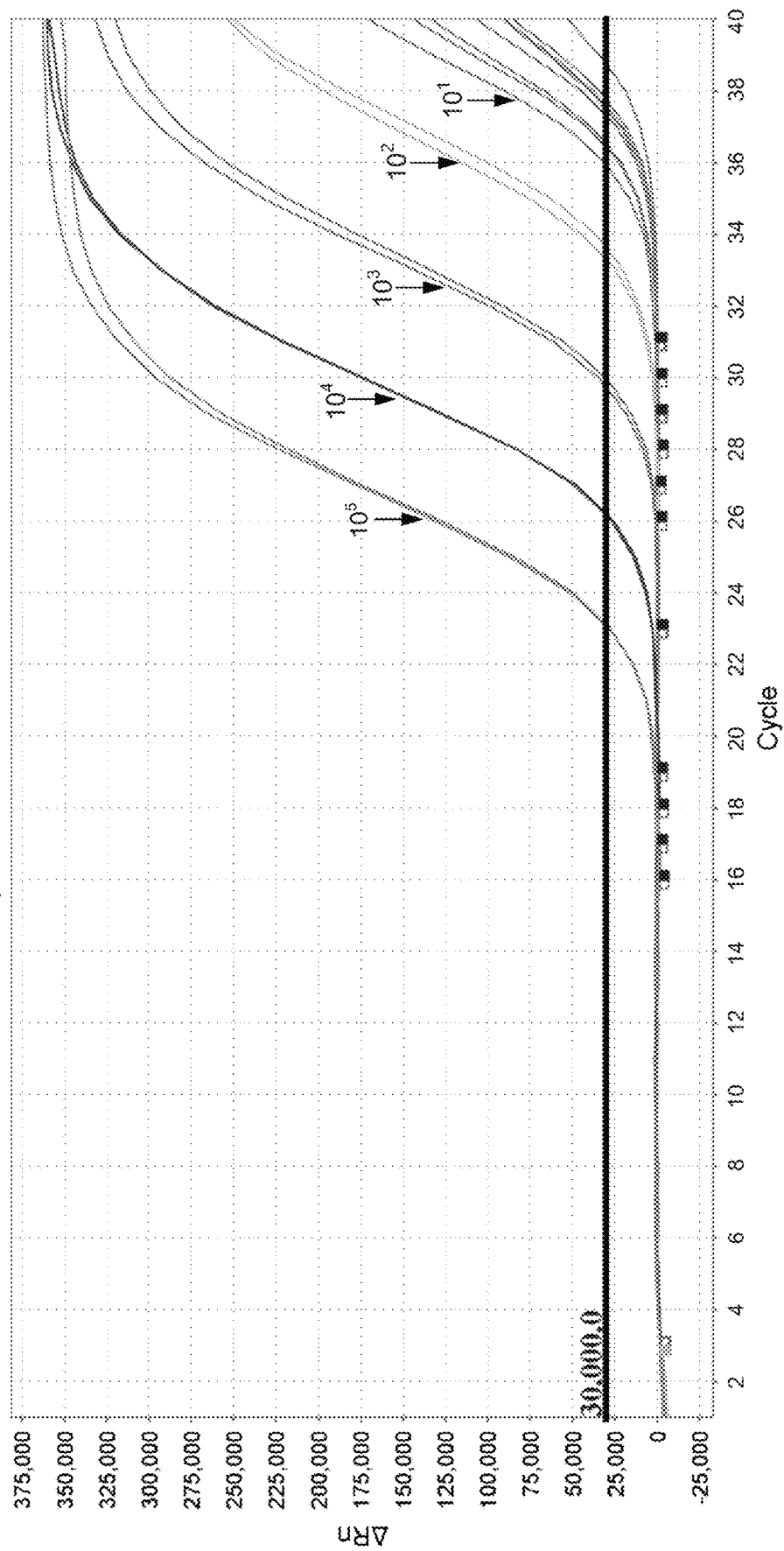
FIGS. 7A and 7B show the amplification of different copies of HSV2 and the corresponding linearity assay.
Figure 7B:
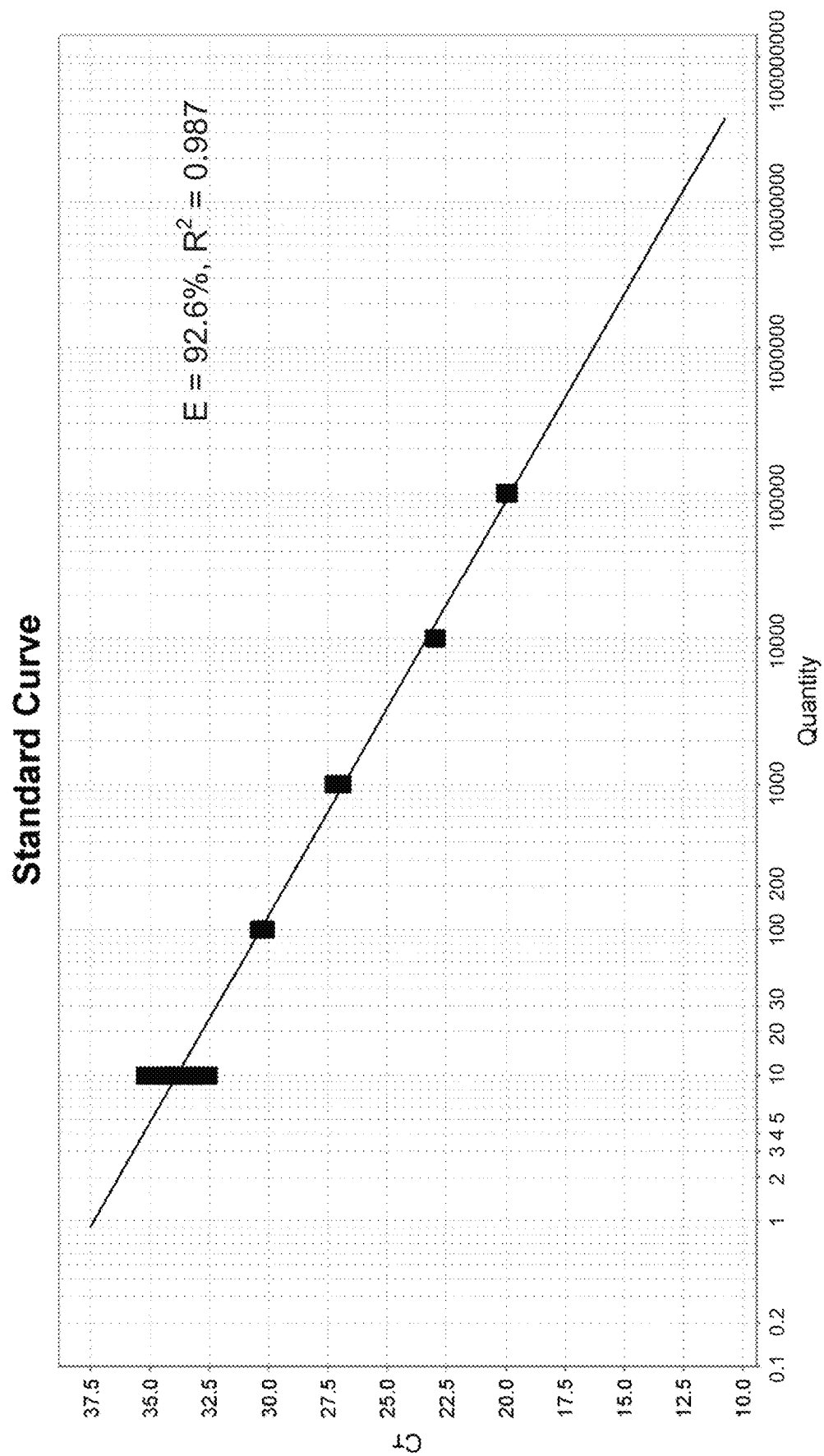

Moreover, the present invention allows for the detection of up to a few copies and the quantitation of the number of copies of HSV1 or HSV2 DNA, while using the rapid thermocycling profile. FIGS. 6A and 6B show the amplification of different copies of HSV1 and the corresponding linearity assay. FIGS. 7A and 7B show the amplification of different copies of HSV2 and the corresponding linearity assay. The sensitivity, efficiency and linearity of the assay conditions were maintained between 10 to $10^5$ copies of DNA. From FIGS. 6A and 7A, it is shown that the assay has high sensitivity. From FIGS. 6B and 7B, the efficiency of the amplification was found to be 100.6% and 92.6% with a $R^2$ value of 0.994 and 0.987 for HSV1 and HSV2, respectively. As the $R^2$ values are close to the theoretical optimum of 1.0, and therefore the assay could be expanded to a quantitative assay to estimate gene copies in a clinical setting.

In conclusion, the present invention provides kits and methods for detecting HSV1 and/or HSV2 using real-time PCR with specific primers and probes. The present invention allows for the detection of both HSV1 and HSV2 DNA in the same reaction. The present invention has advantages of high specificity and high sensitivity, and can be used for quantitative detection. Moreover, the present invention has the advantage of reduced reaction time, which significantly decreases the extension time without compromising on specificity or sensitivity. Therefore, the present invention provides a rapid, sensitive and specific diagnosis of HSV infections, so as to treat HSV infections and prevent HSV transmissions effectively.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A method for simultaneously or independently detecting HSV1 and/or HSV2, the method comprising the step of amplifying DNA from HSV1 and/or HSV2 using real-time polymerase chain reaction with at least one primer pair specific to HSV1 and/or HSV2,
   wherein the primer pair specific to HSV1 consists of a forward primer of SEQ ID NO: 1 and a reverse primer of SEQ ID NO: 2, or consists of a forward primer of SEQ ID NO: 4 and a reverse primer of SEQ ID NO: 7; and
   wherein the primer pair specific to HSV2 consists of a forward primer of SEQ ID NO: 6 and a reverse primer of SEQ ID NO: 7.

2. The method according to claim 1 wherein a probe specific to HSV1 is used in the real-time polymerase chain reaction and has a sequence of SEQ ID NO: 3, or a sequence complementary to SEQ ID NO: 3.

3. The method according to claim 1 wherein a probe specific to HSV1 is used in the real-time polymerase chain reaction and has a sequence of SEQ ID NO: 5, or a sequence complementary to SEQ ID NO: 5.

4. The method according to claim 1 wherein a probe specific to HSV2 is used in the real-time polymerase chain reaction and has a sequence of SEQ ID NO: 8 or a sequence complementary to SEQ ID NO: 8.

* * * * *